United States Patent
Montagnier et al.

(10) Patent No.: US 7,309,589 B2
(45) Date of Patent: Dec. 18, 2007

(54) SENSITIVE DETECTION OF BACTERIA BY IMPROVED NESTED POLYMERASE CHAIN REACTION TARGETING THE 16S RIBOSOMAL RNA GENE AND IDENTIFICATION OF BACTERIAL SPECIES BY AMPLICON SEQUENCING

(75) Inventors: Luc Montagnier, New York, NY (US); Claude Lavallee, Lexington, MA (US)

(73) Assignee: Vironix LLC, New York, NY (US)

( * ) Notice: Subject to any disclaimer, the term of this patent is extended or adjusted under 35 U.S.C. 154(b) by 0 days.

(21) Appl. No.: 11/204,854

(22) Filed: Aug. 16, 2005

(65) Prior Publication Data

US 2006/0057616 A1     Mar. 16, 2006

Related U.S. Application Data

(60) Provisional application No. 60/603,120, filed on Aug. 20, 2004.

(51) Int. Cl.
- C12P 19/34 (2006.01)
- C12Q 1/68 (2006.01)
- C07H 21/04 (2006.01)

(52) U.S. Cl. .................... 435/91.2; 435/6; 435/91.5; 536/24.33

(58) Field of Classification Search .............. None
See application file for complete search history.

(56) References Cited

U.S. PATENT DOCUMENTS

| | | |
|---|---|---|
| 5,310,874 A | 5/1994 | Tamura et al. |
| 5,518,901 A | 5/1996 | Murtagh |
| 5,589,570 A | 12/1996 | Tamura et al. |
| 5,593,836 A | 1/1997 | Niemiec et al. |
| 5,643,723 A | 7/1997 | Persing et al. |
| 5,656,740 A | 8/1997 | Gross et al. |
| 5,658,749 A | 8/1997 | Thornton |
| 5,660,981 A | 8/1997 | Gross et al. |
| 5,677,124 A | 10/1997 | DuBois et al. |
| 5,688,646 A | 11/1997 | Montagnier et al. |
| 5,688,669 A | 11/1997 | Murtagh |
| 5,693,467 A | 12/1997 | Roblin et al. |
| 5,707,802 A | 1/1998 | Sandhu et al. |
| 5,734,086 A | 3/1998 | Scott et al. |
| 5,744,306 A | 4/1998 | Murtagh et al. |
| 5,747,257 A | 5/1998 | Jensen |
| 5,750,387 A | 5/1998 | Hodgson et al. |
| 5,763,169 A | 6/1998 | Sandhu et al. |
| 5,763,246 A | 6/1998 | Hodgson et al. |
| 5,776,750 A | 7/1998 | Hodgson et al. |
| 5,786,197 A | 7/1998 | Lonetto |
| 5,789,217 A | 8/1998 | Hodgson et al. |
| 5,795,976 A | 8/1998 | Oefner et al. |
| 5,830,670 A | 11/1998 | de la Monte et al. |
| 5,843,654 A | 12/1998 | Heisler et al. |
| 5,843,669 A | 12/1998 | Kaiser et al. |
| 5,851,764 A | 12/1998 | Fisher et al. |
| 5,854,067 A * | 12/1998 | Newgard et al. ........... 435/366 |
| 5,876,924 A | 3/1999 | Zhang et al. |
| 5,882,643 A | 3/1999 | Lonetto |
| 5,888,736 A * | 3/1999 | Lacroix et al. ................ 435/6 |
| 5,907,085 A | 5/1999 | Gonsalves et al. |
| 5,912,117 A | 6/1999 | Dodge et al. |
| 5,919,625 A | 7/1999 | DuBois et al. |
| 5,922,538 A | 7/1999 | Hazel et al. |
| 5,939,262 A | 8/1999 | Pasloske et al. |
| 5,942,391 A | 8/1999 | Zhang et al. |
| 5,948,634 A | 9/1999 | de la Monte et al. |
| 5,948,888 A | 9/1999 | de la Monte et al. |
| 5,958,693 A | 9/1999 | Sandhu et al. |
| 5,976,805 A | 11/1999 | You |
| 5,985,557 A | 11/1999 | Prudent et al. |
| 5,994,066 A | 11/1999 | Bergeron et al. |
| 6,001,564 A | 12/1999 | Bergeron et al. |
| 6,001,567 A | 12/1999 | Brow et al. |
| 6,022,687 A | 2/2000 | Letarte et al. |
| 6,025,132 A | 2/2000 | Jannes et al. |
| 6,033,858 A | 3/2000 | Bastian |
| 6,090,543 A | 7/2000 | Prudent et al. |

(Continued)

FOREIGN PATENT DOCUMENTS

| EP | 1371736 A1 * | 12/2003 |
| WO | WO 9513396 A2 * | 5/1995 |

OTHER PUBLICATIONS

Buck et al. (1999) Design strategies and performance of custom DNA sequencing primers. Biotechniques. vol. 27(3): 528-536.*
Neefs et al. (1990) Compilation of small ribosomal subunit RNA sequences. Nucleic Acids Research. vol. 18, S2237-S2317.*
Kajander, et al., "Comparison of Staphylococci and novel Bacteria-Like Particles from blood", Zbl. Bakt. Suppl. 26, 1994.
Akerman, "Scanning Electron Microscopy of Nanobacteria-Novel Biofilm Producting Organisms in Blood", Scanning vol. 15, Suppl. III (1993).
Cifticioglu, et al., "Apoptotic effect of nanobacteria on cultured mammalian cells", Mol. Biol. Cell. Suppl., vol. 7 (1996) 517a.
Cifticioglu, et al., "A new potential threat in antigen and antibody products: Nanobacteria", Vaccines 97, Brown et al. Ed., Cold Spring HarborLaboratory Press, New York 1997.
Baseman, et al., "Mycoplasmas: Sophisticated, Reemerging, and Burdened by their Notoriety", EID vol. 3, No. 1, www.cdc.gov/ncidod/EID/vol3no. 1/baseman.htm, pub date=1997.
Reiman; "Detection and Identification of Previously Unrecognized Microbial Pathogens", EID vol. 4, No. 3, 1997=pub date.

*Primary Examiner*—Jeffrey Fredman
*Assistant Examiner*—Angela Bertagna
(74) *Attorney, Agent, or Firm*—Milde & Hoffberg LLP

(57) ABSTRACT

A method for identifying an RNA form of a bacteria, comprising reverse transcribing RNA material; conducting PCR using primers for a first highly conserved genetic sequence generic of the bacteria; conducting nested PCR using primers for a second highly conserved genetic sequence within the first genetic sequence of the bacteria; and identifying the bacteria based on unconserved amplified sequences linked to the conserved sequences.

7 Claims, No Drawings

U.S. PATENT DOCUMENTS

| | | |
|---|---|---|
| 6,103,468 A | 8/2000 | Russell et al. |
| 6,146,846 A | 11/2000 | McDevitt et al. |
| 6,146,863 A | 11/2000 | Palmer et al. |
| 6,156,537 A | 12/2000 | Fueyo et al. |
| 6,162,618 A | 12/2000 | Warren |
| 6,162,619 A | 12/2000 | Biswas et al. |
| 6,165,764 A | 12/2000 | Holmes et al. |
| 6,165,991 A | 12/2000 | Biswas et al. |
| 6,165,992 A | 12/2000 | Biswas et al. |
| 6,168,797 B1 | 1/2001 | Biswas et al. |
| 6,180,339 B1 | 1/2001 | Sandhu et al. |
| 6,190,881 B1 | 2/2001 | Black et al. |
| 6,194,145 B1 | 2/2001 | Heidrich et al. |
| 6,194,170 B1 | 2/2001 | Wallis |
| 6,197,300 B1 | 3/2001 | Fueyo et al. |
| 6,197,549 B1 | 3/2001 | Nicholas et al. |
| 6,204,014 B1 | 3/2001 | Chalker et al. |
| 6,210,880 B1 | 4/2001 | Lyamichev et al. |
| 6,214,548 B1 | 4/2001 | Relman et al. |
| 6,214,982 B1 | 4/2001 | Pasloske et al. |
| 6,221,582 B1 | 4/2001 | Giesendorf et al. |
| 6,228,584 B1 | 5/2001 | Burnham |
| 6,228,625 B1 | 5/2001 | Biswas et al. |
| 6,238,882 B1 | 5/2001 | Fedon et al. |
| 6,238,887 B1 | 5/2001 | Beattie et al. |
| 6,238,900 B1 | 5/2001 | Hodgson et al. |
| 6,245,542 B1 | 6/2001 | Biswas et al. |
| 6,245,750 B1 | 6/2001 | Shepard |
| 6,245,891 B1 | 6/2001 | Biswas et al. |
| 6,248,329 B1 | 6/2001 | Chandrashekar et al. |
| 6,248,519 B1 | 6/2001 | Engel et al. |
| 6,248,721 B1 | 6/2001 | Chang |
| 6,251,607 B1 | 6/2001 | Tsen et al. |
| 6,251,629 B1 | 6/2001 | Warren |
| 6,251,631 B1 | 6/2001 | Biswas et al. |
| 6,252,130 B1 | 6/2001 | Federoff |
| 6,255,075 B1 | 7/2001 | Huang et al. |
| 6,258,778 B1 | 7/2001 | Rodgers et al. |
| 6,261,769 B1 | 7/2001 | Everett et al. |
| 6,261,773 B1 | 7/2001 | Segawa et al. |
| 6,261,802 B1 | 7/2001 | Huang et al. |
| 6,268,142 B1 | 7/2001 | Duff et al. |
| 6,268,177 B1 | 7/2001 | Biswas et al. |
| 6,270,762 B1 | 8/2001 | Burnham et al. |
| 6,274,361 B1 | 8/2001 | Biswas et al. |
| 6,274,719 B1 | 8/2001 | Biswas et al. |
| 6,277,595 B1 | 8/2001 | Konstantinidis et al. |
| 6,277,830 B1 | 8/2001 | Ganguly et al. |
| 6,287,779 B1 | 9/2001 | Engel et al. |
| 6,287,804 B1 | 9/2001 | Black |
| 6,287,807 B1 | 9/2001 | Wallis |
| 6,294,357 B1 | 9/2001 | Kallender et al. |
| 6,294,652 B1 | 9/2001 | Biswas et al. |
| 6,300,072 B1 | 10/2001 | Jensen |
| 6,300,073 B1 * | 10/2001 | Zhao et al. ............... 435/6 |
| 6,300,091 B1 | 10/2001 | Patton et al. |
| 6,303,771 B1 | 10/2001 | Biswas et al. |
| 6,306,653 B1 | 10/2001 | Papsidero et al. |
| 6,309,866 B1 | 10/2001 | Warren |
| 6,312,903 B1 | 11/2001 | Jannes et al. |
| 6,312,922 B1 | 11/2001 | Edwards et al. |
| 6,312,932 B1 | 11/2001 | Powell |
| 6,326,172 B1 | 12/2001 | Biswas et al. |
| 6,329,138 B1 | 12/2001 | DeBeenhouwer et al. |
| 6,331,411 B1 | 12/2001 | Gwynn et al. |
| 6,339,151 B1 | 1/2002 | Shepard et al. |
| 6,340,564 B1 | 1/2002 | Ingraham et al. |
| 6,346,397 B1 | 2/2002 | Warren et al. |
| 6,348,314 B1 | 2/2002 | Prudent et al. |
| 6,348,328 B1 | 2/2002 | Black et al. |
| 6,348,582 B1 | 2/2002 | Black et al. |
| 6,350,600 B1 | 2/2002 | Biswas et al. |
| 6,353,093 B1 | 3/2002 | Burnham et al. |
| 6,361,965 B1 | 3/2002 | Powell |
| 6,368,600 B1 | 4/2002 | Chandrashekar et al. |
| 6,372,424 B1 | 4/2002 | Brow et al. |
| 6,387,617 B1 | 5/2002 | Asher et al. |
| 6,399,307 B1 | 6/2002 | Pasloske et al. |
| 6,399,343 B1 | 6/2002 | Biswas et al. |
| 6,399,373 B1 | 6/2002 | Bouguelaret |
| 6,403,093 B1 | 6/2002 | Persing et al. |
| 6,403,564 B1 | 6/2002 | Ganguly et al. |
| 6,410,286 B1 | 6/2002 | Hodgson et al. |
| 6,423,499 B1 | 7/2002 | Song et al. |
| 6,432,649 B1 | 8/2002 | Stich et al. |
| 6,432,703 B1 | 8/2002 | Kallender |
| 6,436,399 B1 | 8/2002 | Rikihisa et al. |
| 6,444,876 B1 | 9/2002 | Lassner et al. |
| 6,448,037 B1 | 9/2002 | Holmes et al. |
| 6,451,601 B1 | 9/2002 | Baetge et al. |
| 6,458,535 B1 | 10/2002 | Hall et al. |
| 6,458,572 B1 | 10/2002 | Holmes et al. |
| 6,458,584 B1 | 10/2002 | Mirzabekov et al. |
| 6,475,990 B1 | 11/2002 | Enoki et al. |
| 6,489,110 B1 | 12/2002 | Oudshoorn et al. |
| 6,489,139 B1 | 12/2002 | Kallender et al. |
| 6,492,113 B1 | 12/2002 | Vojdani |
| 6,495,325 B1 | 12/2002 | vanHaeringen et al. |
| 6,495,661 B1 | 12/2002 | Glisson et al. |
| 6,503,747 B2 | 1/2003 | Kathariou et al. |
| 6,518,020 B1 | 2/2003 | Jensen |
| 6,521,426 B1 | 2/2003 | Ciliberto et al. |
| 6,524,795 B1 | 2/2003 | Francis et al. |
| 6,531,148 B1 | 3/2003 | Enoki et al. |
| 6,531,648 B1 | 3/2003 | Lanahan et al. |
| 6,537,774 B1 | 3/2003 | Huang et al. |
| 6,545,140 B1 | 4/2003 | Harmon et al. |
| 6,548,633 B1 | 4/2003 | Edwards et al. |
| 6,555,338 B1 | 4/2003 | Black et al. |
| 6,555,357 B1 | 4/2003 | Kaiser et al. |
| 6,558,902 B1 | 5/2003 | Hillenkamp |
| 6,558,905 B1 | 5/2003 | van Dijk et al. |
| 6,558,909 B2 | 5/2003 | Jensen |
| 6,558,953 B1 | 5/2003 | Gonsalves et al. |
| 6,562,611 B1 | 5/2003 | Kaiser et al. |
| 6,562,957 B1 | 5/2003 | Letarte et al. |
| 6,569,647 B1 | 5/2003 | Zhang et al. |
| 6,573,068 B1 | 6/2003 | Milne Edwards et al. |
| 6,583,266 B1 | 6/2003 | Smith et al. |
| 6,593,086 B2 | 7/2003 | Zhang |
| 2001/0010912 A1 | 8/2001 | Black et al. |
| 2001/0014670 A1 | 8/2001 | Balin et al. |
| 2001/0016334 A1 | 8/2001 | Wallis |
| 2001/0020010 A1 | 9/2001 | Biswas et al. |
| 2001/0023064 A1 | 9/2001 | Biswas et al. |
| 2001/0027183 A1 | 10/2001 | Burnham et al. |
| 2002/0004580 A1 | 1/2002 | Fueyo et al. |
| 2002/0004581 A1 | 1/2002 | Palmer et al. |
| 2002/0025516 A1 | 2/2002 | Black et al. |
| 2002/0048789 A1 | 4/2002 | Huang et al. |
| 2002/0052472 A1 | 5/2002 | Beattie et al. |
| 2002/0058799 A1 | 5/2002 | Biswas et al. |
| 2002/0082234 A1 | 6/2002 | Black et al. |
| 2002/0091237 A1 | 7/2002 | Biswas et al. |
| 2002/0098544 A1 | 7/2002 | Black |
| 2002/0102700 A1 | 8/2002 | Biswas et al. |
| 2002/0106776 A1 | 8/2002 | Biswas et al. |
| 2002/0115075 A1 | 8/2002 | Biswas et al. |
| 2002/0119454 A1 | 8/2002 | Lyamichev et al. |
| 2002/0119510 A1 | 8/2002 | Biswas et al. |
| 2002/0119520 A1 | 8/2002 | Konstantinidis et al. |
| 2002/0120116 A1 | 8/2002 | Kunsch et al. |
| 2002/0123047 A1 | 9/2002 | Burnham |
| 2002/0127596 A1 | 9/2002 | Biswas et al. |

| | | | | | | |
|---|---|---|---|---|---|---|
| 2002/0128437 A1 | 9/2002 | Fedon et al. | | 2003/0131377 A1 | 7/2003 | Anderson et al. |
| 2002/0146751 A1 | 10/2002 | Kallender et al. | | 2003/0134275 A1 | 7/2003 | Long et al. |
| 2002/0146790 A1 | 10/2002 | Wallis | | 2003/0134293 A1 | 7/2003 | Liu |
| 2002/0150963 A1 | 10/2002 | Biswas et al. | | 2003/0134295 A1 | 7/2003 | Herrmann et al. |
| 2002/0160447 A1 | 10/2002 | Huang et al. | | 2003/0134301 A1 | 7/2003 | Brooksbank et al. |
| 2002/0162123 A1 | 10/2002 | Chang | | 2003/0134310 A1 | 7/2003 | Cujec |
| 2003/0017532 A1 | 1/2003 | Biswas et al. | | 2003/0134343 A1 | 7/2003 | Batra et al. |
| 2003/0027286 A1 | 2/2003 | Haselbeck et al. | | 2003/0135879 A1 | 7/2003 | Weeks et al. |
| 2003/0044796 A1 | 3/2003 | Neri et al. | | 2003/0138772 A1 | 7/2003 | Gao et al. |
| 2003/0044864 A1 | 3/2003 | Short et al. | | 2003/0138783 A1 | 7/2003 | Sukumar et al. |
| 2003/0054338 A1 | 3/2003 | Dahlberg et al. | | 2003/0138798 A1 | 7/2003 | Stone et al. |
| 2003/0059771 A1 | 3/2003 | Clark et al. | | 2003/0138803 A1 | 7/2003 | Brooksbank et al. |
| 2003/0065156 A1 | 4/2003 | Williams et al. | | 2003/0138816 A1 | 7/2003 | Sahali et al. |
| 2003/0082614 A1 | 5/2003 | Biswas et al. | | 2003/0138854 A1 | 7/2003 | Boel et al. |
| 2003/0108873 A1 | 6/2003 | Dahlberg et al. | | 2003/0138925 A1 | 7/2003 | Keith et al. |
| 2003/0118992 A1 | 6/2003 | Warren | | 2003/0139590 A1 | 7/2003 | Bonini et al. |
| 2003/0124545 A1 | 7/2003 | Rothman et al. | | 2003/0143202 A1 | 7/2003 | Binley et al. |
| 2003/0124613 A1 | 7/2003 | Hildebrand et al. | | 2003/0143219 A1 | 7/2003 | Madison et al. |
| 2003/0124673 A1 | 7/2003 | Fesik et al. | | 2003/0143241 A1 | 7/2003 | Reyes et al. |
| 2003/0125248 A1 | 7/2003 | Hair et al. | | 2003/0143531 A1 | 7/2003 | vanHaeringen et al. |
| 2003/0125258 A1 | 7/2003 | Lanctor et al. | | 2003/0143534 A1 | 7/2003 | Goswami et al. |
| 2003/0125269 A1 | 7/2003 | Li | | 2003/0143537 A1 | 7/2003 | Schuetz et al. |
| 2003/0125524 A1 | 7/2003 | Novak et al. | | 2003/0143553 A1 | 7/2003 | Sommer |
| 2003/0125539 A1 | 7/2003 | Bonini et al. | | 2003/0143577 A1 | 7/2003 | Hogrefe et al. |
| 2003/0129202 A1 | 7/2003 | Trepo et al. | | 2003/0143593 A1 | 7/2003 | Hermitte et al. |
| 2003/0129577 A1 | 7/2003 | Sheppard | | 2003/0143600 A1 | 7/2003 | Gocke et al. |
| 2003/0129589 A1 | 7/2003 | Koster et al. | | 2003/0143618 A1 | 7/2003 | Hatzfield et al. |
| 2003/0129599 A1 | 7/2003 | Sharma et al. | | 2003/0143671 A1 | 7/2003 | Adler et al. |
| 2003/0129631 A1 | 7/2003 | Pasternack et al. | | 2003/0143684 A1 | 7/2003 | Gerard et al. |
| 2003/0129667 A1 | 7/2003 | Giese et al. | | 2003/0144234 A1 | 7/2003 | Burton et al. |
| 2003/0129687 A1 | 7/2003 | Ruben et al. | | 2003/0144490 A1 | 7/2003 | Edwards et al. |
| 2003/0129702 A1 | 7/2003 | Smith et al. | | 2003/0145347 A1 | 7/2003 | Lanahan et al. |
| 2003/0129724 A1 | 7/2003 | Grozinger et al. | | | | |
| 2003/0129746 A1 | 7/2003 | Maertens et al. | | | | |
| 2003/0131375 A1 | 7/2003 | Conner et al. | | | | |

* cited by examiner

SEQUENCE LISTING

<160> NUMBER OF SEQ ID NOS: 8

<210> SEQ ID NO 1
<211> LENGTH: 18
<212> TYPE: DNA
<213> ORGANISM: Artificial
<220> FEATURE:
<223> OTHER INFORMATION: PCR primer Moll Outer (sense)

<400> SEQUENCE: 1
aaygggtgag taacacgt                                                 18

<210> SEQ ID NO 2
<211> LENGTH: 19
<212> TYPE: DNA
<213> ORGANISM: artificial
<220> FEATURE:
<223> OTHER INFORMATION: PCR Primer Moll Outer Primer (antisense)

<400> SEQUENCE: 2
cccgagaacg tattcaccg                                                19

<210> SEQ ID NO 3
<211> LENGTH: 18

```
<212> TYPE: DNA
<213> ORGANISM: artificial
<220> FEATURE:
<223> OTHER INFORMATION: PCR Primer Moll Inner Primer (sense)

<400> SEQUENCE: 3
ctacgggagg cagcagta                                               18

<210> SEQ ID NO 4
<211> LENGTH: 24
<212> TYPE: DNA
<213> ORGANISM: artificial
<220> FEATURE:
<223> OTHER INFORMATION: PCR Primer Moll Inner Primer (antisense)

<400> SEQUENCE: 4
gtatctaatc ctrtttgctc ccca                                        24

<210> SEQ ID NO 5
<211> LENGTH: 19
<212> TYPE: DNA
<213> ORGANISM: artificial
<220> FEATURE:
<223> OTHER INFORMATION: PCR Primer Bact Outer Primer (antisense)

<400> SEQUENCE: 5
cccgrgaacg tattcacsg                                              19

<210> SEQ ID NO 6
<211> LENGTH: 24
<212> TYPE: DNA
<213> ORGANISM: artificial
<220> FEATURE:
<223> OTHER INFORMATION: PCR Primer Bact Inner Primer (sense)

<400> SEQUENCE: 6
ctacgggagg cwgcagtrrg gaat                                        24

<210> SEQ ID NO 7
<211> LENGTH: 27
<212> TYPE: DNA
<213> ORGANISM: artificial
<220> FEATURE:
<223> OTHER INFORMATION: PCT Primer Bact Inner Primer (antisense)

<400> SEQUENCE: 7
wgggtatcta atcctrtttg mtccccw                                     27

<210> SEQ ID NO 8
<211> LENGTH: 18
<212> TYPE: DNA
<213> ORGANISM: artificial
<220> FEATURE:
<223> OTHER INFORMATION: PCR Primer Gneg Outer Primer (sense)

<400> SEQUENCE: 8
raygggtgag taaygymt                                               18
```

SENSITIVE DETECTION OF BACTERIA BY IMPROVED NESTED POLYMERASE CHAIN REACTION TARGETING THE 16S RIBOSOMAL RNA GENE AND IDENTIFICATION OF BACTERIAL SPECIES BY AMPLICON SEQUENCING

This application claims benefit under 35 U.S.C. 119(e) to Provisional Application 60/603,120, filed on Aug. 20, 2004.

FIELD OF THE INVENTION

The present invention relates to the field of PCR methods, and specific primers therefore, as well as their use in the identification of any type of bacteria, and in particular RNA forms of bacteria.

BACKGROUND OF THE INVENTION

The use of biological fluids for therapeutic human application such as plasmas, albumin, live vaccines, stem cells requires that they are absolutely devoid of bacterial contamination. It has been found that filtering, and possibly other traditional methods, may fail to eliminate all forms of organisms, leading to possible contamination or experimental artifacts.

It is believed that certain pathologies are associated with bacteria or bacterial forms which are difficult to detect, and which may pass through nano-porous barriers. This leads to possible errors in diagnosis or causation, and which may lead to erroneous treatment and impede prevention.

See, Hopert, Anne, Uphoff, Cord C., Wirth, Manfred, Hauser, Hansjorg, and Drexler, Hans G., "Specificity and sensitivity of Polymerase Chain Reaction (PCR) in comparison with other methods for the detection of *mycoplasma* contamination in cell lines", J. Immunological Methods, 164(1993):91-100, expressly incorporated herein by reference.

Kajander, E. O., et al., "Comparison of *Staphylococci* and novel Bacteria-Like Particles from blood", Zbl. Bakt. Suppl. 26, 1994, expressly incorporated herein by reference.

Akerman, Kari K., "Scanning Electron Microscopy of Nanobacteria—Novel Biofilm Producing Organisms in Blood", Scanning Vol. 15, Suppl. III (1993), expressly incorporated herein by reference. www.newcastle.edu.au/discipline/biology/projects/hons_cpru.html, expressly incorporated herein by reference.

Cifticioglu, Neva, et al., "Apoptotic effect of nanobacteria on cultured mammalian cells", Mol. Biol. Cell. Suppl., Vol. 7 (1996):517a Cifticioglu, Neva, et al., "A new potential threat in antigen and antibody products: Nanobacteria", Vaccines 97, Brown et al. Ed., Cold Spring Harbor Laboratory Press, New York, 1997, expressly incorporated herein by reference.

Baseman, Joel B., et al., "*Mycoplasmas*: Sophisticated, Reemerging, and Burdened by their Notoriety", EID Vol. 3, N° 1 www.cdc.gov/ncidod/EID/vol3no1/baseman.htm, expressly incorporated herein by reference.

Relman, David A., "Detection and Identification of Previously Unrecognized Microbial Pathogens", EID Vol. 4, N° 3 www.cdc.gov/ncidod/EID/vol4no3/relman.htm, expressly incorporated herein by reference.

Mattman, Lida H., Cell Wall Deficient Forms-Stealth Pathogens, 2nd Ed., CRC Press (1993), expressly incorporated herein by reference.

U.S. Pat. No. 5,688,646, expressly incorporated herein by reference, describes novel *mycoplasmas* which are prominent in patients who are thought to be suffering from AIDS. Devices are also provided for the in vitro detection of *mycoplasmas* in biological fluid by means of a reagent which is specific for the *mycoplasma* group without being specific for particular species within said group. Devices for testing *mycoplasma* sensitivity to antibiotics are also described.

See the following, each of which and cited references is expressly incorporated herein by reference in their entirety:

| Pat. No | Title |
| --- | --- |
| 6,562,611 | FEN-1 endonucleases, mixtures and cleavage methods |
| 6,558,902 | Infrared matrix-assisted laser desorption/ionization mass spectrometric analysis of macromolecules |
| 6,555,357 | FEN-1 endonuclease, mixtures and cleavage methods |
| 6,555,338 | NrdF from *Staphylococcus aureus* |
| 6,537,774 | UPS (undecaprenyl diphosphate synthase |
| 6,492,113 | Detection of *Mycoplasma* genus and species in patients with chronic fatigue syndrome and fibromyalgia |
| 6,489,139 | FabZ from *Staphylococcus aureus* |
| 6,489,110 | EF-Tu mRNA as a marker for viability of bacteria |
| 6,458,572 | Phosphatidylglycerophosphate synthase from *Staphylococcus aureus* |
| 6,458,535 | Detection of nucleic acids by multiple sequential invasive cleavages 02 |
| 6,448,037 | PgsA |
| 6,432,703 | RATC from *Streptococcus pneumoniae* |
| 6,410,286 | Asparaginyl tRNA synthetase from *Staphylococcus Aureus* |
| 6,399,343 | inFB |
| 6,372,424 | Rapid detection and identification of pathogens |
| 6,361,965 | YfiI pseudouridine synthase |
| 6,353,093 | gidB |
| 6,350,600 | trmD |
| 6,348,582 | Prokaryotic polynucleotides polypeptides and their uses |
| 6,348,328 | Compounds |
| 6,348,314 | Invasive cleavage of nucleic acids |
| 6,346,397 | GyrA |
| 6,340,564 | yhxB |
| 6,331,411 | TopA |
| 6,326,172 | ytgP |
| 6,312,932 | Yfil pseudouridine synthase |
| 6,309,866 | 6-phosphogluconate dehydrogenase |
| 6,303,771 | Pth |

-continued

| Pat. No | Title |
| --- | --- |
| 6,294,652 | Response regulator |
| 6,294,357 | FabF from *Staphylococcus aureus* |
| 6,287,807 | MurF |
| 6,287,804 | nrdG |
| 6,277,595 | FabZ |
| 6,274,719 | Gcp |
| 6,274,361 | pth |
| 6,270,762 | tdk |
| 6,268,177 | Isolated nucleic acid encoding nucleotide pyrophosphorylase |
| 6,261,802 | Ups (ugc) |
| 6,261,769 | Intergenic spacer target sequence for detecting and distinguishing *Chlamydial* species or strains |
| 6,255,075 | BirA |
| 6,251,631 | nadE from *Streptococcus pneumoniae* |
| 6,251,629 | ABC transporter |
| 6,248,721 | Method of using mouse model for evaluation of HIV vaccines |
| 6,245,891 | nusB polypeptides and polynucleotides and methods thereof |
| 6,245,542 | tRNA methyltransferase from *Streptococcus pneumoniae* |
| 6,238,900 | Polynucleotides encoding glutamyltrna synthetase from *staphylococcus aureus* |
| 6,238,887 | Ribosome recycling factor (FRR) of *Staphylococcus aureus* |
| 6,238,882 | GidA1 |
| 6,228,625 | metK from *Streptococcus pneumoniae* |
| 6,228,584 | DexB |
| 6,210,880 | Polymorphism analysis by nucleic acid structure probing with structure-bridging oligonucleotides |
| 6,204,014 | DnaB |
| 6,197,549 | Ama |
| 6,197,300 | ftsZ |
| 6,194,170 | MurF of *Streptococcus pneumoniae* |
| 6,190,881 | Ribonucleotide diphosphate reductase, nrdF, of *streptococcus pneumoniae* |
| 6,168,797 | FabF |
| 6,165,992 | Histidine kinase |
| 6,165,991 | Sensor histidine kinase of *Streptococcus pneumoniae* |
| 6,165,764 | Polynucleotides encoding tRNA methyl transferases from *Streptococcus pneumoniae* |
| 6,162,619 | Sensor histidine kinase of *streptococcus pneumoniae* |
| 6,162,618 | 6-phosphogluconate dehydrogenase of *Streptococcus pneumoniae* |
| 6,156,537 | Phospho-N-acetylmuramoyl-pentapeptide transferase of *Streptococcus pneumoniae* |
| 6,146,863 | *Staphylococcus aureus* 3-hydroxyacyl-CoA dehydrogenase |
| 6,146,846 | Primosome protein a of *streptococcus pneumoniae* |
| 6,140,079 | GidB |
| 6,140,061 | Response regulator |
| 6,111,074 | PyrH of *Streptococcus pneumoniae* |
| 6,110,723 | Yfii pseudouridine synthase |
| 6,110,685 | infB |
| 6,090,543 | Cleavage of nucleic acids |
| 6,060,294 | Alanyl tRNA synthetase from *Staphylococcus aureus* |
| 6,001,567 | Detection of nucleic acid sequences by invader-directed cleavage |
| 5,994,111 | Leucyl tRNA synthetase from *staphylococcus aureus* |
| 5,985,557 | Invasive cleavage of nucleic acids |
| 5,882,643 | Lep |
| 5,851,764 | Human prostate tumor inducing gene-1 and uses thereof |
| 5,843,669 | Cleavage of nucleic acid acid using thermostable *methoanococcus jannaschii* FEN-1 endonucleases |
| 5,843,654 | Rapid detection of mutations in the p53 gene |
| 5,795,976 | Detection of nucleic acid heteroduplex molecules by denaturing high-performance liquid chromatography and methods for comparative sequencing |
| 5,789,217 | DNA encoding asparaginyl tRNA synthetase from *staphylococcus aureus* |
| 5,786,197 | Lep |
| 5,776,750 | Alanyl tRNA synthetase polynucleoyides of *staphylococcus* |
| 5,763,246 | DNA encoding arginyl tRNA synthetase from *staphylococcus aureus* |
| 5,750,387 | DNA encoing leucyl TRNA synthetase from *staphylococcus aureus* |
| 5,688,646 | *Mycoplasmas*-agents for detecting and characterizing *mycoplasmas* in vitro (See above) |
| 6,562,957 | Genomic sequence encoding endoglin and fragments thereof |
| 6,545,140 | DNA encoding an avian beta-defensin and uses thereof |
| 6,531,148 | Therapeutic agents |
| 6,495,661 | DNA encoding the outer membrane protein of *Pasteurella multocida* |
| 6,475,990 | Drugs, foods or drinks with the use of algae-derived physiologically active substances |
| 6,451,601 | Transiently immortalized cells for use in gene therapy |
| 6,403,564 | Ribavirin-interferon alfa combination therapy for eradicating detectable HCV-RNA in patients having chronic hepatitis C infection |
| 6,399,373 | Nucleic acid encoding a retinoblastoma binding protein (RBP-7) and polymorphic markers associated with said nucleic acid |
| 6,368,600 | Parasitic helminth cuticlin nucleic acid molecules and uses thereof |
| 6,339,151 | Enzyme catalyzed therapeutic agents |
| 6,277,830 | 5'-amino acid esters of ribavirin and the use of same to treat hepatitis C with interferon |
| 6,258,778 | Methods for accelerating bone and cartilage growth and repair |

-continued

| Pat. No | Title |
| --- | --- |
| 6,248,329 | Parasitic helminth cuticlin nucleic acid molecules and uses thereof |
| 6,245,750 | Enzyme catalyzed therapeutic agents |
| 6,022,687 | Diagnosis of and therapy for hereditary haemorrhagic telangiectasia |
| 6,593,086 | Nucleic acid amplification methods |
| 6,583,266 | Nucleic acid and amino acid sequences relating to *mycobacterium tuberculosis* and leprae for diagnostics and therapeutics |
| 6,573,068 | Claudin-50 protein |
| 6,569,647 | Nucleic acid amplification method: ramification-extension amplification method (RAM) |
| 6,562,611 | FEN-1 endonucleases, mixtures and cleavage methods |
| 6,558,953 | Grapevine leafroll virus proteins and their uses |
| 6,558,909 | Haemobartonella PCR methods and materials |
| 6,558,905 | Diagnostics and therapeutics for osteoporosis |
| 6,558,902 | Infrared matrix-assisted laser desorption/ionization mass spectrometric analysis of macromolecules |
| 6,555,357 | FEN-1 endonuclease, mixtures and cleavage methods |
| 6,548,633 | Complementary DNA's encoding proteins with signal peptides |
| 6,531,648 | Grain processing method and transgenic plants useful therein |
| 6,524,795 | Diagnostics for cardiovascular disorders |
| 6,521,426 | Preparation of recombinant adenovirus carrying a rep gene of adeno-associated virus |
| 6,518,020 | Haemobartonella PCR methods and materials |
| 6,503,747 | Serotype-specific probes for Listeria monocytogenes |
| 6,495,325 | Detection and quantification of micro-organisms using amplification and restriction enzyme analysis |
| 6,458,584 | Customized oligonucleotide microchips that convert multiple genetic information to simple patterns, are portable and reusable |
| 6,458,535 | Detection of nucleic acids by multiple sequential invasive cleavages 02 |
| 6,444,876 | Acyl CoA: cholesterol acyltransferase related nucleic acid sequences |
| 6,436,399 | Nucleic acid encoding the major outer membrane protein of the causative agent of human granulocytic ehrlichiosis and peptides encoded thereby |
| 6,432,649 | Methods for detecting *Ehrlichia canis* and *Ehrlichia chaffeensis* in vertebrate and invertebrate hosts |
| 6,423,499 | PCR primers for detection and identification of plant pathogenic species, subspecies, and strains of acidovorax |
| 6,403,093 | Methods to detect granulocytic ehrlichiosis |
| 6,399,307 | Methods of quantifying viral load in an animal with a ribonuclease resistant RNA preparation |
| 6,387,617 | Catalytic nucleic acid and methods of use |
| 6,372,424 | Rapid detection and identification of pathogens |
| 6,348,314 | Invasive cleavage of nucleic acids |
| 6,329,138 | Method for detection of the antibiotic resistance spectrum of mycobacterium species |
| 6,312,922 | Complementary DNAs |
| 6,312,903 | Simulataneous detection, identification and differentiation of eubacterial taxa using a hybridization assay |
| 6,306,653 | Detection and treatment of breast disease |
| 6,300,091 | Herbicide target genes and methods |
| 6,300,072 | PCR methods and materials for detecting *bartonella* species |
| 6,287,779 | Detection of fermentation-related microorganisms |
| 6,268,142 | Diagnostics and therapeutics for diseases associated with an IL-1 inflammatory haplotype |
| 6,261,773 | Reagent for nucleic acid amplification and process for nucleic acid amplification |
| 6,252,130 | Production of somatic mosaicism in mammals using a recombinatorial substrate |
| 6,251,607 | PCR primers for the rapid and specific detection of *Salmonella typhimurium* |
| 6,248,519 | Detection of fermentation-related microorganisms |
| 6,221,582 | Polynucleic acid sequences for use in the detection and differentiation of prokaryotic organisms |
| 6,214,982 | Ribonuclease resistant RNA preparation and utilization |
| 6,214,548 | Diagnostic methods for Cyclospora |
| 6,194,145 | Genus and species-specific identification of *Legionella* |
| 6,180,339 | Nucleic acid probes for the detection and identification of fungi |
| 6,103,468 | Rapid two-stage polymerase chain reaction method for detection of lactic acid bacteria in beer |
| 6,090,543 | Cleavage of nucleic acids |
| 6,033,858 | Detection of transmissible spongiform encephalopathies |
| 6,025,132 | Probes targeted to rRNA spacer regions, methods and kits for using said probes, for the detection of respiratory tract pathogens |
| 6,001,567 | Detection of nucleic acid sequences by invader-directed cleavage |
| 6,001,564 | Species specific and universal DNA probes and amplification primers to rapidly detect and identify common bacterial pathogens and associated antibiotic resistance genes from clinical specimens for routine diagnosis in microbiology laboratories |
| 5,994,066 | Species-specific and universal DNA probes and amplification primers to rapidly detect and identify common bacterial pathogens and associated antibiotic resistance genes from clinical specimens for routine diagnosis in microbiology laboratories |
| 5,985,557 | Invasive cleavage of nucleic acids |
| 5,976,805 | Neisseria gonorrhoeae specific DNA fragment-GC3 |
| 5,958,693 | Extraction of DNA by boiling cells in an alkaline phenol/guanidine thiocyanate solution |

-continued

| Pat. No | Title |
|---|---|
| 5,948,888 | Neural thread protein gene expression and detection of Alzheimer's disease |
| 5,948,634 | Neural thread protein gene expression and detection of Alzheimer's disease |
| 5,942,391 | Nucleic acid amplification method: ramification-extension amplification method (RAM) |
| 5,939,262 | Ribonuclease resistant RNA preparation and utilization |
| 5,922,538 | Genetic markers and methods for the detection of *Listeria monocytogenes* and *Listeria* spp |
| 5,919,625 | Ribonuclease resistant viral RNA standards |
| 5,912,117 | Method for diagnosis of lyme disease |
| 5,907,085 | Grapevine leafroll virus proteins and their uses |
| 5,876,924 | Nucleic acid amplification method hybridization signal amplification method (HSAM) |
| 5,843,669 | Cleavage of nucleic acid acid using thermostable *methoanococcus jannaschii* FEN-1 endonucleases |
| 5,830,670 | Neural thread protein gene expression and detection of Alzheimer's disease |
| 5,795,976 | Detection of nucleic acid heteroduplex molecules by denaturing high-performance liquid chromatography and methods for comparative sequencing |
| 5,763,169 | Nucleic acid probes for the detection and identification of fungi |
| 5,747,257 | Genetic markers and methods for the detection of *escherichia coli* serotype-0157:H7 |
| 5,744,306 | Methods for nucleic acid detection, sequencing, and cloning using exonuclease |
| 5,734,086 | Cytochrome P450.sub.lpr gene and its uses |
| 5,707,802 | Nucleic acid probes for the detection and identification of fungi |
| 5,693,467 | Mycoplasma polymerase chain reaction testing system using a set of mixed and single sequence primers |
| 5,688,669 | Methods for nucleic acid detection, sequencing, and cloning using exonuclease |
| 5,677,124 | Ribonuclease resistant viral RNA standards |
| 5,660,981 | Selection of diagnostic genetic markers in microorganisms and use of a specific marker for detection of *salmonella* |
| 5,658,749 | Method for processing *mycobacteria* |
| 5,656,740 | Nucleic acid fragments useful in the detection of *Salmonella* |
| 5,643,723 | Detection of a genetic locus encoding resistance to rifampin in *mycobacterial* cultures and in clinical specimens |
| 5,593,836 | Primers and probes for detecting *Pneumocystis carinii* |
| 5,589,570 | Integrin alpha subunit cytoplasmic domain polypeptides and methods |
| 5,518,901 | Methods for adapting nucleic acid for detection, sequencing, and cloning using exonuclease |
| 5,310,874 | Integrin .alpha. subunit cytoplasmic domain polypeptides and antibodies |
| 20030124545 | Quantitative assay for the simultaneous detection and speciation of bacterial infections |
| 20030118992 | ABC transporter |
| 20030108873 | Systems for the detection of target sequences |
| 20030082614 | Map |
| 20030065156 | Novel human genes and gene expression products I |
| 20030059771 | Compositions and methods related to the Rig tumor suppressor gene and protein |
| 20030054338 | Detection of target sequences by cleavage of non-target nucleic acids |
| 20030044864 | Cellular engineering, protein expression profiling, differential labeling of peptides, and novel reagents therefor |
| 20030044796 | Reactions on dendrimers |
| 20030027286 | Bacterial promoters and methods of use |
| 20030017532 | ndp |
| 20020162123 | Combination immunogene therapy |
| 20020160447 | Ups (ugc) |
| 20020150963 | Map |
| 20020146790 | MurF |
| 20020146751 | fabF |
| 20020128437 | GidA1 |
| 20020127596 | murF2 |
| 20020123047 | dexB |
| 20020120116 | *Enterococcus faecalis* polynucleotides and polypeptides |
| 20020119520 | FabZ |
| 20020119510 | gcp |
| 20020119454 | Polymorphism analysis by nucleic acid structure probing with structure-bridging oligonucleotides |
| 20020115075 | nadE |
| 20020106776 | pth |
| 20020102700 | metK |
| 20020098544 | nrdG |
| 20020091237 | nusB |
| 20020082234 | Novel prokaryotic polynucleotides, polypeptides and their uses |
| 20020058799 | Novel pth |
| 20020052472 | ama |
| 20020048789 | birA |
| 20020025516 | NRDE |
| 20020004581 | gcp |
| 20020004580 | ftsZ |
| 20010027183 | tdk |
| 20010023064 | yfjO |
| 20010020010 | Histidine kinase |
| 20010016334 | MurF |

| Pat. No | Title |
| --- | --- |
| 20010014670 | Treatment and diagnosis of Alzheimer's disease |
| 20010010912 | nrdF |
| 20030145347 | Grain processing method and transgenic plants useful therein |
| 20030144490 | Extended cDNAs for secreted proteins |
| 20030144234 | Methods for the treatment of chronic pain and compositions therefor |
| 20030143684 | Method of identifying inhibitors of C—C chemokine receptor 3 |
| 20030143671 | Novel beta-defensins |
| 20030143618 | Method for easy cloning and selection of chimeric DNA molecules |
| 20030143600 | Detection of extracellular tumor-associated nucleic acid in blood plasma or serum using nucleic acid amplification assays |
| 20030143593 | Quantative method for measuring gene expression |
| 20030143577 | High fidelity DNA polymerase compositions and uses therefor |
| 20030143553 | Nucleic acid amplification with direct sequencing |
| 20030143537 | Genotyping assay to predict CYP3A5 phenotype |
| 20030143534 | Probes for myctophid fish and a method for developing the same |
| 20030143531 | Detection and quantification of microorganisms using amplification and restriction enzyme analysis |
| 20030143241 | Hepatitis E virus vaccine and method |
| 20030143219 | Nucleic acid molecules encoding a transmembrane serine protease 25, the encoded polypeptides and methods based thereon |
| 20030143202 | Anemia |
| 20030139590 | DNA encoding SNORF25 receptor |
| 20030138925 | Novel human gene relating to respiratory diseases, obesity, and inflammatory bowel disease |
| 20030138854 | Method for determining BAGE expression |
| 20030138816 | Methods and kits for diagnosing the occurrence or the phase of minimal change nephrotic syndrome (MCNS) in a human |
| 20030138803 | Identification and use of molecules implicated in pain |
| 20030138798 | Macular degeneration diagnostics and therapeutics |
| 20030138783 | Aberrantly methylated genes as markers of breast malignancy |
| 20030138772 | Method of detecting and/or identifying adeno-associated virus (AAV) sequences and isolating novel sequences identified thereby |
| 20030135879 | Methods and materials for making and using transgenic dicamba-degrading organisms |
| 20030134343 | Specific mucin expression as a marker for pancreatic cancer |
| 20030134310 | Cellular kinase targets and inhibitors, and methods for their use |
| 20030134301 | Identification and use of molecules implicated in pain |
| 20030134295 | Method for detection of pathogenic organisms |
| 20030134293 | Method for rapid and accurate identification of microorganisms |
| 20030134275 | Telomerase reverse transcriptase (TERT) genes |
| 20030131377 | DNA molecules from maize and methods of use thereof |
| 20030131375 | Plant regulatory sequences for selective control of gene expression |
| 20030129746 | Epitopes in viral envelope proteins and specific antibodies directed against these epitopes: use for detection of HCV viral antigen in host tissue |
| 20030129724 | Class II human histone deacetylases, and uses related thereto |
| 20030129702 | DNA encoding galanin GALR2 receptors and uses thereof |
| 20030129687 | Keratinocyte growth factor-2 |
| 20030129667 | Method of diagnosing transmissible spongiform encephalopathies |
| 20030129631 | Gene family with transformation modulating activity |
| 20030129599 | Human hematopoietic growth regulatory gene and uses |
| 20030129589 | DNA diagnostics based on mass spectrometry |
| 20030129577 | Kunitz domain polypeptide Zkun8 |
| 20030129202 | Mutated hepatitis b virus, its nucleic and protein constituents and uses thereof |
| 20030125539 | DNA encoding SNORF25 receptor |
| 20030125524 | Novel cytokine zalphal 1 ligand |
| 20030125269 | T-type calcium channel |
| 20030125258 | Bone polypeptide-1 |
| 20030125248 | Novel bone mineralization proteins, DNA, vectors expression systems |
| 20030124673 | Site-specific isotopically-labeled proteins, amino acids, and biochemical precursors therefor |
| 20030124613 | Epitope testing using soluble HLA |

SUMMARY OF THE INVENTION

The present invention allows improved detection of such bacterial contaminants, including unconventional forms such as filtering forms (nanoforms), nanobacteria, and L-forms.

Its principal applications are the:

Detection of very low levels of mycoplasma contamination of cell lines and biological fluids Identification of latent bacterial infections in various pathologies Detection of live forms passing through filters having a pore size of between 100 and 20 nm Direct detection of RNA-containing subunits of bacteria.

Different primers have been designed:

MOLL primers have been designed initially to detect mollicutes (*mycoplasma*) species based on the conserved regions of the 16 s ribosomal RNA gene. In fact they can also detect gram positive bacteria 1) Moll Outer Primer (sense)        SEQ ID NO:1 (AAYGGGTGAGTAACACGT), 2) Moll Outer Primer (antisense)    SEQ ID NO:2 (CCCGAGAACGTATTCACCG)

3) Moll Inner Primer (sense)        SEQ ID NO:3 (CTACGGGAGGCAGCAGTA)

4) Moll Inner Primer (antisense)    SEQ ID NO:4 (GTATCTAATCCTRTTTGCTCCCCA)

BACT primers will detect gram positive and gram negative bacteria. The sequence of MOLL primers is included in the degenerated sequence of the BACT primers.

1) Bact Outer Primer (antisense)    SEQ ID NO:5 (CCCGRGAACGTATTCACSG),

2) Bact Inner Primer (sense)        SEQ ID NO:6 (CTACGGGAGGCWGCAGTRRGGAAT),

3) Bact Inner Primer (antisense)    SEQ ID NO:7 (WGGGTATCTAATCCTRTTTGMTCCCCW)

The GNEG set of primers is specific of gram negative bacteria. It differs from the Moll 16 out S by a single nucleotide 1) Gneg Outer Primer (sense) SEQ ID NO: 8 (RAYGGGTGAGTAAYGYMT), The present invention therefore provides a method for identifying an RNA form of a bacteria, comprising reverse transcribing RNA material; conducting PCR using primers for a first highly conserved genetic sequence generic of the bacteria; conducting nested PCR using primers for a second highly conserved genetic sequence within the first amplified genetic sequence of the bacteria; and identifying the bacteria based on unconserved amplified sequences linked to the conserved sequences.

It is believed that the Nanoforms are a stable, low metabolic rate form of bacteria, which may be related to pathology, which have characteristic DNA which is generally undetectable by PCR or nested PCR. However, these organisms do have characteristic RNA, and therefore these can be detected by nested RT-PCR. Likewise, because these are now detectable according to the present invention, it is therefore possible to monitor and optimize treatments directed toward clearing these from infected subjects.

It is believed that Nanoforms are involved in human pathology, and further that these low metabolic organisms are involved in a constellation of chronic human diseases. Further, it is believed that some of these Nanoforms may be subcellular, that is, incomplete, and therefore may require association with other Nanoform, or other organisms or cells, for replication or reconstitution as a complete DNA bacterial form. Preliminary evidence suggests that the genetic material within a single Nanoforms is insufficient to reconstitute the entirety of a related bacterial (DNA) form, and therefore that multiple Nanoforms may be required in order to be self-replicating for the complete organism.

For example, multiple Nanoforms may infect a single cell, together constituting a complete genome for the associated DNA bacteria. Reverse transcriptase activity, for example, due to retroviruses, endogenous retroviral sequences, DNA pol I activity, etc., may be sufficiently active to generate the bacterial genome.

These Nanoforms may be biologically associated with retroviruses, such as HIV, which would therefore increase their likelihood of replication, since they would then carry their own reverse transcriptase, and potentially account for replication of sub-cellular fragments. The retroviruses may be passengers within the Nanoforms, and the Nanoforms represent an infectious particle for the virus.

The present invention reveals that the Nanoforms retain conserved sequences of 16S rRNA, and therefore may be targeted on this basis, for example by tetracycline analog antibiotics, especially administered over extended durations.

DETAILED DESCRIPTION OF THE PREFERRED EMBODIMENTS

Material and Methods

Oligonucleotide Primers.

The oligonucleotide primers used were:

1) Moll Outer Primer (sense)        SEQ ID NO:1 (AAYGGGTGAGTAACACGT),

2) Gneg Outer Primer (sense)        SEQ ID NO:8 (RAYGGGTGAGTAAYGYMT),

3) Bact Outer Primer (antisense)    SEQ ID NO:5 (CCCGRGAACGTATTCACSG),

4) Bact Inner Primer (sense)        SEQ ID NO:6 (CTACGGGAGGCWGCAGTRRGGAAT), and

5) Bact Inner Primer (antisense)    SEQ ID NO:7 (WGGGTATCTAATCCTRTTTGMTCCCCW)

where R = G or A, S = G or C, W = A or T, M = A or C, and Y = T or C.

Expected lengths of amplicons are ~200 bp and ~450 bp with the outer and inner primers, respectively. The primers employed were formulated as equal amounts of each primer within the class identified by the sequence.

Nucleic Acid Preparation and PCR/RT-PCR.

Cell line supernatants (400 µl), human plasma (200-400µl) and human peripheral blood mononuclear cells (PBMC, 3-10 millions cells) were lyzed with 10 mMTris, pH7.4, 10 mM EDTA, 150 mM NaCl, 0.4% SDS, and 10 µg Proteinase K at 60° C. for 1 h. Nucleic samples were extracted three times with one volume of phenol/chloroform and one time with chloroform and precipitated by addition of 1/10 volume of 3M sodium acetate and two volumes of ethanol at −60° C. for 1 h. Samples were centrifuged 30 mm. and the nucleic acid pellets were washed with 70% cold ethanol and solubilized in 10 mM Tris-HCI, pH 8.0. These preparations were stored at −60° C.

PCR reaction mix (50 µl) consisted of 5 mM MgCl2, 50 mM Tris, pH 8.0, 15 mM (NH4)2SO4, 10 mM B-Mercaptoethanol, 500 µM dATP, dCTP, dGTP, and DTTP, 0.025% BSA, 1 µM of each outer primer, 1 U Taq polymerase (Roche Molecular biochemicals, Laval, Canada), and 5-10 µl nucleic acid sample. For the first round PCR, the denaturation, annealing, and elongation temperatures and times used were 95° C. for 30 s, 42° C. for 30 s, and 78° C. for 2 m, respectively, for 42 cycles. After the final cycle, the products were kept at 78° C. for 10 m. One µl of the PCR product was subjected to a second round PCR with the set of inner primers. Denaturation, annealing, and elongation temperatures and times used were 95° C. for 30 s, 47° C. for 30 s, and 78° C. for 1 m, respectively, for 42 cycles, followed by a single incubation at 78° C. for 10 m. After the first and second round PCR, 10 µl of PCR product was analyzed by gel electrophoresis using 1.5% agarose, stained with ethidium bromide, visualized under ultraviolet light and photographed. Visible bands with appropriate size were cut and sequenced using the inner primers (DNA Landmarks, St-Jean sur le Richelieu, Canada). Sequence homology search was performed using the BLAST program of the NIH web site.

Samples negative for the appropriate band by PCR were subjected to a first round RT-PCR followed by a second round PCR. RT-PCR reaction mix (50 µl) consisted of 5 mM MgCl2, 50 mM Tris, pH 8.0, 15 mM (NH4)2SO4, 10 mM B-Mercaptoethanol, 500 µM dATP, dCTP, dGTP, and DTTP, 0.025% BSA, 1 µM of each outer primer, and Titan enzyme mix (Roche Molecular biochemicals, Laval, Canada), and 5 µl nucleic acid sample. The reverse transcription step was performed at 42° C. for 30 m. The first and second rounds PCR were performed as described above.

The precautions addressed elsewhere (Kwok and Higuchi, 1989) were followed to minimize the risk of false-positive results caused by the carry-over of previously amplified DNA. For example, extraction of nucleic acids and preparation of PCR/RT-PCR mix were performed under a sterile flow bench, only aliquoted reagents and filter tips were used, and negative controls were incorporated into each run.

Results

All Samples:
First round PCR/RT-PCR: no detection of expected amplicon (~1,200 bp).
Second round PCR (nested-PCR): all amplicon (~450 bp) sequences related to bacterial 16S ribosomal RNA gene.

Patients' Lymphocytes (18 Samples):
No 450 bp amplicon detected by nested-PCR from first round PCR.
All samples positive (450 bp) by nested-PCR from RT-PCR.
Therefore, bacteria are in an "RNA state", and are referred to herein as "Nanoforms".

Samples of Patients' Plasma:
11 samples/12 positive for 450 bp amplicon by nested-PCR from first round PCR.

Discussion

Cell wall deficient pathogenic microorganisms, which may be *mycoplasma*, so-called L-forms, or potentially other types, are difficult to detect. Therefore, their involvement in pathology may be vastly under-reported.

It has been found, however, that these organisms have a well-conserved RNA sequences, such as the 16S rRNA, even when corresponding DNA or RNA is undetectable by a traditional polymerase chain reaction (PCR) or reverse transcriptase PCR (RT-PCR) method, which may be detected by nested RT-PCR amplification, using primers according to the present invention.

The present invention therefore provides a sensitive and specific method for detecting bacterial forms, which may be called "Nanoforms", even when traditional methods fail. This therefore allows diagnosis of pathogens previously unrecognized, and monitoring of treatment thereof.

What is claimed is:

1. A method for amplifying genetic sequences, comprising the steps of:
(1) first, reverse transcribing RNA to DNA, and conducting PCR using at least one outer primer having a sequence:

SEQ ID NO: 1 (AAYGGGTGAGTAACACGT) for Gram positive bacteria or,

SEQ ID NO: 8 (RAYGGGTGAGTAAYGYMT) for Gram negative bacteria, and at least one primer having a sequence:

SEQ ID NO: 5 (CCCGRGAACGTATTCACSG), (2) second, conducting nested PCR, using inner primers, comprising at least one primer having a sequence:
SEQ ID NO: 6 (CTACGGGAGGCWGCAGTRRG-GAAT), and at least one primer having a sequence:
SEQ ID NO: 7 (WGGGTATCTAATCCTRTTTGMTC-CCCW), wherein R=G or A, S=G or C, W=A or T, M=A or C, and Y=T or C.

2. The method according to claim 1 further comprising the step of identifying an organism corresponding to an amplicon resulting from said nested PCR step.

3. A kit, comprising a unit amount of each of the following combinations of primer sequences, substantially absent interfering DNA primer sequences, sufficient for a PCR identification of a bacteria in a biological sample:
(a) (i) at least one sequence selected from the group consisting of:
SEQ ID NO: 1 (AAYGGGTGAGTAACACGT) and SEQ ID NO: 8 (RAYGGGTGAGTAAYGYMT), and
(ii) SEQ ID NO: 5 (CCCGRGAACGTATTCACSG); and
(b) SEQ ID NO: 6 (CTACGGGAGGCWGCAGTRRG-GAAT), and SEQ ID NO: 7 (WGGGTATCTAATC-CTRTTTGMTCCCCW),
wherein R=G or A, S=G or C, W=A or T, M=A or C, and Y=T or C,
wherein said component (a) further comprises a reverse transcriptase (RNA-dependent, DNA polymerase) activity, and deoxynucleotide triphosphates.

4. The kit according to claim 3, wherein said component (b) further comprises temperature resistant, DNA-dependent DNA polymerase activity, and deoxynucleotide triphosphates.

5. The kit according to claim 3, wherein at least one of said component (a) and (b) comprises 5 mM MgCl2, 50 mM Tris, pH 8.0, 15 mM (NH4)2SO4, 10 mM B-Mercaptoethanol, 500 μM dATP, dCTP, dGTP, and dTTP, 0.025% BSA, 1 μM of each primer, a reverse transcriptase (RNA dependent DNA polymerase) activity, and a temperature resistant, DNA-dependent DNA polymerase activity.

6. A method for using the kit according to claim 3 for amplifying genetic sequences, comprising the steps of:
(1) first, reverse transcribing RNA to DNA, and conducting PCR using at least one outer primer having a sequence:
SEQ ID NO: 1 (AAYGGGTGAGTAACACGT) for Gram positive bacteria or, SEQ ID NO: 8 (RAYGGGTGAGTAAYGYMT) for Gram negative bacteria, and at least one primer having a sequence:
SEQ ID NO: 5 (CCCGRGAACGTATTCACSG),
(2) second, conducting nested PCR, using inner primers, comprising at least one primer having a sequence:
SEQ ID NO: 6 (CTACGGGAGGCWGCAGTRRG-GAAT), and at least one primer having a sequence:
SEQ ID NO: 7 (WGGGTATCTAATCCTRTTTGMTC-CCCW),
wherein R=G or A, S=G or C, W=A or T, M=A or C, and Y=T or C.

7. The method according to claim 6 further comprising the step of identifying an organism corresponding to an amplicon resulting from said nested PCR step.

* * * * *